United States Patent [19]

Kneller et al.

[11] Patent Number: 5,075,502

[45] Date of Patent: Dec. 24, 1991

[54] NONIONIC X-RAY CONTRAST AGENTS, COMPOSITIONS AND METHODS

[75] Inventors: Mills T. Kneller, University City; Youlin Lin, Chesterfield; James R. Wheatley, Hazelwood, all of Mo.

[73] Assignee: Mallinckrodt, Inc., St. Louis, Mo.

[21] Appl. No.: 450,693

[22] Filed: Dec. 13, 1989

[51] Int. Cl.$^5$ .................. A61K 49/04; C07H 3/00; C07C 103/78
[52] U.S. Cl. ........................................ 564/153; 424/5
[58] Field of Search ......................................... 564/153

[56] References Cited

U.S. PATENT DOCUMENTS

| | | | |
|---|---|---|---|
| 4,001,323 | 1/1977 | Felder et al. | 260/559 A |
| 4,021,481 | 5/1977 | Almen et al. | 260/558 A |
| 4,239,747 | 12/1980 | Pfeiffer et al. | 424/5 |
| 4,352,788 | 10/1982 | Felder et al. | 424/5 |
| 4,364,921 | 12/1982 | Speck et al. | 424/5 |

FOREIGN PATENT DOCUMENTS 0049745 4/1982 European Pat. Off.
0317492 5/1989 European Pat. Off.

OTHER PUBLICATIONS

Speck et al., Chem. Abstracts, vol. 111, No. 15; 133794u (1989).
Felder et al., Chem. Abstracts, vol. 110, No. 21; 192447k (1989).
Pfeiffer et al., Chem. Abstracts, vol. 97, No. 17; 144596z (1982).
Haanaldsen et al., Chem. Abstracts, vol. 100, No. 1; 6000e (1984).
Simo et al., Chem. Abstracts, vol. 102, No. 1; 5958c (1985).
Sovak et al., Chem. Abstracts, vol. 108, No. 10; 82096w (1988).

*Primary Examiner*—Johann Richter
*Attorney, Agent, or Firm*—Rita E. Downard

[57] ABSTRACT

Triiodinated isophthalamide derivatives, useful as X-ray contrast agents, having at least one amide group derived from the amino-alcohol, 3-(N-2-hydroxyethyl)amino-1,2-propanediol, which provides high water solubility and low mammalian toxicity, and methods of preparing them. Methods of preparing 3-(N-2-hydroxyethyl)amino-1,2-propanediol are provided.

13 Claims, No Drawings

NONIONIC X-RAY CONTRAST AGENTS, COMPOSITIONS AND METHODS

FIELD OF THE INVENTION

This invention relates to novel X-ray contrast agents, methods of preparing them, radiological compositions containing such agents, and methods for X-ray visualization utilizing such compositions.

BACKGROUND OF THE INVENTION

Nonionic contrast agents for intravascular and central nervous system visualization are complex molecules. As is known, the iodine in the molecule provides opacification to the X-rays, while the remainder of the molecule provides the framework for transport of the iodine atoms. However, the structural arrangement of the molecule is important in providing stability, solubility and biological safety in various organs. A stable carbon-iodine bond is achieved in most compounds by attaching it to an aromatic nucleus. An enhanced degree of solubility as well as safety is conferred on the molecule by the addition of suitable solubilizing and detoxifying groups. Further, nonionic contrast agents are particularly desirable compared to contemporary ionic agents due to the minimization of those pharmacological effects associated with colligative properties, e.g., osmolality.

Several of the features that are desirable for intravascular and central nervous system nonionic contrast agents are often incompatible so that all such agents represent compromises. In searching for the best compromise, the controlling factors are pharmacological inertness, i.e., in vivo safety, and high water solubility. Thus, the ideal intravascular or central nervous system nonionic agent represents a compromise in an attempt to obtain the following criteria: (1) maximum opacification to X-rays; (2) pharmacological inertness; (3) high water solubility; (4) stability; (5) selective excretion; (6) low viscosity; and (7) minimal osmotic effects.

Illustrative nonionic contrast agents include N,N'-bis(2,3-dihydroxypropyl)-5-N-(2-hydroxyethyl)-glycolamido-2,4,6-triiodoisophthalamide (Lin, U.S. Pat. No. 4,396,598) and 5-N-(2,3-dihydroxypropyl)acetamido-2,4,6-triiodo-N,N'-bis(2,3-dihydroxypropyl)isophthalamide (Nordal et al., U.S. Pat. No. 4,250,113 and Rakli et al. U.S. Pat. No. 4,396,597).

There is a continuing need for nonionic contrast agents which meet all or substantially all of the foregoing criteria. It is an object of the present invention to provide nonionic X-ray contrast agents which substantially meet these criteria. It is a further object of this invention to provide nonionic X-ray contrast agents with improved pharmacological inertness, i.e., low toxicity, by means of the incorporation of highly hydrophilic side chains. It is a still further object of this invention to provide chemically stable nonionic X-ray contrast agents having low osmolality. Other objects and features will be in part apparent and in part pointed out hereinafter.

SUMMARY OF THE INVENTION

Briefly, the present invention is directed to compounds of the formula:

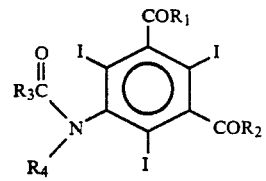

wherein $R_1$ is $N(CH_2CH_2OH)CH_2CHOHCH_2OH$; $R_2$ equals $R_1$, $NHCH_3$, $NHCH_2CH_2OH$, or $NHCH_2CHOHCH_2OH$; $R_3$ equals $CH_3$, $CH_2CH_3$, $CH_2OH$, $CH(CH_3)OH$, $CH(CH_3)OCH_3$, $CHOHCH_2OH$, $CH_2OCH_3$, or $CH_2OCH_2CH_3$; $R_4$ equals H, $CH_3$, $CH_2CH_2OH$, $CH_2CH_2OCH_3$, $CH_2CHOHCH_2OH$, or $CH_2CHOHCH_2OCH_3$; or $R_3$, $R_4$, and the 5-N together form the group

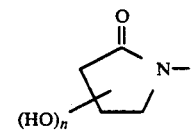

wherein n equals 0-3, preferably 0 or 1.

The present invention is also directed to dimers of the above compound connected at the 5-N position by means of a diamide, thus:

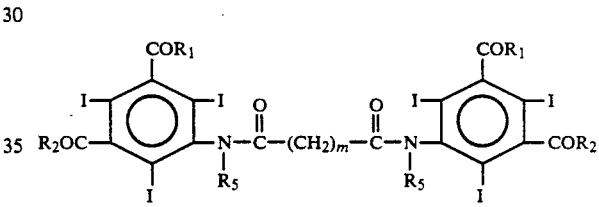

wherein $R_1$ and $R_2$ have the meanings given above; $R_5$ is H, $CH_3$, $CH_2CH_2OH$, $CH_2CHOHCH_2OH$, and $CH_2OCH_3$; and m equals 0-4, preferably 0-2.

The present invention is further directed to methods for making such compounds by incorporation of an aminoalcohol, 3-(N-2-hydroxyethyl)amino-1,2-propanediol, and methods of making this aminoalcohol. The invention is also directed to radiological compositions containing such compounds and methods for utilizing such compounds in X-ray visualization.

Water solubility and safety of triiodinated aromatic compounds are obtained by attachment of suitable polar and hydrophilic side chains. 3-(N-2-Hydroxyethyl)amino-1,2-propanediol, as in the case of other aminopolyhydroxyl groups, such as 3-amino-1,2-propanediol used for N,N'-bis(2,3-dihydroxypropyl)-5-N-(2-hydroxyethyl)glycolamido-2,4,6-triiodoisophthalamide and 5-N-(2,3-dihydroxypropyl)acetamido-2,4,6-triiodo-N,N'-bis (2,3-dihydroxypropyl)isophthalamide and 2amino-1,3-propanediol used for N,N'-bis(1,3-dihydroxypropyl)L-5-α-hydroxypropionylamino-2,4,6-triiodoisophthalamide, provides good water solubility and in vivo safety for X-ray contrast media. However, an advantage of using 3-(N-2-hydroxyethyl)amino-1,2-propanediol is to provide even higher hydrophilicity for the contrast molecule due to the introduction of an additional hydroxyl group. This highly hydrophilic amino-triol can confer water-solubility and improve the safety of X-ray contrast media.

DETAILED DESCRIPTION OF THE INVENTION

In accordance with the present invention, it has now been found that compounds of the formulas set out above are suitable for use as nonionic X-ray contrast agents. More specifically in the practice of the invention, the compounds may be used as nonionic X-ray contrast agents. These agents may be used in various radiographic procedures including those involving cardiography, coronary arteriography, aortography, cerebral and peripheral angiography, arthrography, intravenous pyelography and urography.

Each of the compounds of the present invention has at least one amide group derived from the aminoalcohol, 3-(N-2-hydroxyethyl)amino-1,2-propanediol. This starting material may be prepared by reacting glycidol with ethanolamine under epoxide-opening conditions or by reacting 3-chloro-1,2-propanediol with ethanolamine under secondary amine-forming conditions and neutralizing the hydrochloride salt thus formed.

Compounds having a 5-hydroxyacetylamino group (5-hydroxyacetamido or 5-glycolamido group) are unstable to basic conditions and will undergo a structural reorganization (known in this case as the Smiles rearrangement) to a phenolic ether. The Smiles rearrangement products are generally insoluble in water and are not, therefore, useful as X-ray contrast agents. In accordance with the present invention, it has been found that the Smiles rearrangement can be avoided when the 5-amino group is either a 5-methoxyacetylamino (methoxyacetamido) or a 5-ethoxyacetylamino moiety to give the compounds of the present invention wherein $R_3$ equals $CH_2OCH_3$ or $CH_2OCH_2CH_3$. The resulting compounds do not undergo the Smiles rearrangement.

In a second, related stability enhancement effect of these methoxylated or ethoxylated agents, U.S. Pat. No. 4,396,597 teaches that compounds with a 5-[N-($\beta$-hydroxyalkyl)acetylamino] group are unstable and undergo a base catalyzed cyclization and iodine elimination which renders this class of compounds less useful as X-ray contrast media. An example of such a compound is 5-N-(2,3-dihydroxypropyl)acetamido-2,4,6,-triiodo-N,N'-bis(2,3-dihydroxypropyl)isophthalamide. The '597 patent further teaches that this problem may be overcome by utilizing a temperature dependent buffer. In accordance with the present invention, it has been found that the cyclization and deiodination problem may also be averted by replacing the 5-N-($\beta$-hydroxyalkyl) group with 5-N-($\alpha$-methoxyalkyl) group. This replacement in compounds of the invention, that is wherein R equals $CH_2CH_2OCH_3$, yields a compound that is stable to cyclization and iodine elimination at near neutral to basic pH.

Compounds of the present invention having a substituted lactam cyclic structure at the 5 position, that is, where $R_3$, $R_4$ and the 5-amido are combined to form

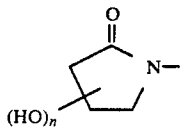

have the added advantage of avoiding both types of instability, rearrangement and cyclization. The hydroxyl substitution of the lactam structure has the advantage of increasing the water solubility as needed for X-ray contrast compounds.

To further improve the osmotic effects of nonionic X-ray contrast media, the present invention also includes dimeric compounds. Hyperosmolality is known to cause vascular pain during the injection of an X-ray contrast agent. Furthermore, high osmolality has been shown to be an important factor in perturbation of the normal heart functions at the time of cardioangiography. The main advantage of the dimers of the present invention is the low osmolality with concomitant low toxicity. This is achieved by highly soluble dimeric compounds having six iodine atoms per molecule as provided by the present invention. At a fixed iodine concentration, these compounds exhibit significantly lower osmotic effects than equivalent monomeric agents due to reduced number of solvated particles in the solution. The dimeric compounds of the present invention provide this advantage while maintaining acceptable solubility characteristics due to the high hydrophilicity of the amine-alcohol side chains.

In further accordance with the present invention, radiological compositions may be prepared containing one of the aforementioned compounds of the invention as an X-ray contrast agent together with a pharmaceutically acceptable radiological vehicle.

Pharmaceutically acceptable radiological vehicles include those that are suitable for injection such as aqueous buffer solutions; e.g., tris(hydroxymethyl)aminomethane (and its salts), phosphate, citrate, bicarbonate, etc., sterile water for injection, physiological saline, and balanced ionic solutions containing chloride and/or bicarbonate salts of normal blood plasma cations such as Ca, Na, K and Mg. Other buffer solutions are described in Remington's Practice of Pharmacy, Eleventh Edition, for example on page 170. The vehicles may contain a chelating amount, e.g., a small amount, of ethylenediamine tetraacetic acid, the calcium disodium salt, or other pharmaceutically acceptable chelating agent.

The concentration of the X-ray contrast agents of the invention in the pharmaceutically acceptable vehicle, for example an aqueous medium, varies with the particular field of use. A sufficient amount is present to provide satisfactory X-ray visualization. For example, when using aqueous solutions for angiography, the concentration of iodine is generally 140–440 mg/ml and the dose is 25–300 ml.

The radiological compositions of the invention may be used in the usual way in X-ray procedures. For example, in the case of selective coronary arteriography, a sufficient amount of the radiological composition to provide adequate visualization is injected into the coronary system and then the system is scanned with a suitable device such as a fluoroscope.

Examples of the compounds of the present invention wherein $R_1$ and $R_2$ are the same are N,N'-bis[(2,3-dihydroxypropyl)-2-hydroxyethyl]-5-acetamido-2,4,6-triiodoisophthalamide; N,N'-bis[(2,3-dihydroxypropyl)-2-hydroxyethyl]-5-hydroxyacetamido-2,4,6-triiodoisophthalamide; N,N'-bis[(2,3-dihydroxypropyl)-2-hydroxyethyl]-5-(2-hydroxy)propionamido-2,4,6-triiodoisophthalamide; N,N'-bis[(2,3-dihydroxypropyl)-2-hydroxyethyl]-5-methoxyacetamido-2,4,6-triiodoisophthalamide; N,N'-bis[(2,3-dihydroxypropyl)-2-hydroxyethyl]-5-[N-(2-hydroxyethyl)hydroxyacetamido]-2,4,6-triiodoisophthalamide; N,N'-bis[(2,3-dihydroxypropyl)-2-hydroxyethyl]-5-[N-(2-hydroxyethyl)acetamido]-2,4,6- triiodoisophthalamide; N,N'-bis[(2,3-dihydroxypropyl)-2-hydroxyethyl]-5-[N-(2-methoxyethyl)acetamido]-2,4,6-triiodoisophthalamide; N,N'-bis[(2,3-dihydroxypropyl)-2-hydroxyethyl]-5-[(N-methyl)hydroxyacetamido]-2,4,6-triiodoisophthalamide; N,N'-bis[(2,3-dihydroxypropyl)-2-hydroxyethyl]-5-[(N-methyl)acetamido]-2,4,6-triiodoisophthalamide; N,N'-bis[(2,3-dihydroxypropyl)-2-hydroxyethyl]-5-N-(2-hydroxybutyrolactamido)-2,4,6-triiodoisophthalamide; N,N'-bis[(2,3-dihydroxypropyl)-2-hydroxyethyl]-5-N-(S-2-hydroxybutyrolactamido)-2,4,6-triiodoisophthalamide; and 5-N-butyrolactamido-N,N'-bis[(2,3-dihydroxypropyl)-2-hydroxyethyl]-2,4,6-triiodoisophthalamide.

These compounds may all be made starting from 5-amino-2,4,6-triiodoisophthaloyl chloride, which may be made from 5-amino-2,4,6-triiodoisophthalic acid, which is disclosed in U.S. Pat. No. 4,396,598, incorporated herein by reference. Generally, the 5-amino group may first be substituted under amide-forming conditions to form the desired amide and the resulting compound reacted with 3-(N-2-hydroxyethyl)amino-1,2-propanediol under amide-forming conditions to add the desired amide to the 1 and 3 carbonyl groups. Examples of the compounds that may be used to react with the 5-amine are acetyl chloride, acetoxyacetyl chloride, 2-acetoxypropionyl chloride, and methoxyacetyl chloride. The acetoxy groups may later be hydrolyzed to produce a hydroxy group by various means, including acid hydrolysis or ion-exchange resins.

Secondary substitution of the 5-amido group (i.e., where $R_4$ is other than hydrogen) is generally preferred to follow addition of the amino-alcohol. Examples of compounds which may be used to react with the 5-amido group under basic, alkylating conditions are alkyl halides, for example, methyl halides, such as methyl iodide; 2-haloethylacetates, such as 2-bromoethylacetate; 2-haloethanols, such as 2-chloroethanol; and 2-haloethyl methyl ethers, such as 2-bromoethyl methyl ether.

The substitution of the 5-amino group to form the cyclic butyrolactamide is also generally preferred to follow addition of the amino-alcohol. Substitution of the amine may be accomplished by the addition, under amide-producing conditions, of various butyryl acid halides, such as 4-chlorobutyryl chloride, 2-acetoxy-4-(methylthio)butyryl chloride, or 2,4-dibromobutyryl bromide. Use of the latter two will result in a hydroxy-substituted lactamide following hydrolysis. Cyclization of the butyramide chain is caused by exposure to cyclizing conditions appropriate to the starting material. For example, when 2-chlorobutyryl chloride is used, the cyclization may be accomplished by using alkaline alcohol mixtures, such as methanol and aqueous sodium hydroxide mixtures. When 2-acetoxy-4-(methylthio)butyryl chloride is used, the methyl iodide of the butyramide is preferably formed first, followed by treatment with alkaline alcohol.

Prior to addition of the butyryl group it is preferred to protect the hydroxyl groups of the amides, preferably by means of acetate groups. This may be simply done by any acetate addition method under suitable protecting conditions, such as by using acetic anhydride under ester-forming conditions, such as in the presence of a base, for example, pyridine. These protecting acetate groups and the one from 2-acetoxy-4-(methylthio)butyryl chloride, if used, can then be removed by hydrolysis utilizing various conditions such as using an aqueous sodium hydroxide and methanol mixture.

When $R_2$ does not equal $R_1$, a different synthetic route is preferred. The $R_2$ substitution is preferably made first, followed by a substitution at the 5-amino group. For example, the intermediate compound 5-amino-2,4,6-triiodo-3-N-methylaminocarbonylbenzoic acid chloride may be used to produce compounds wherein $R_2$ equals $NHCH_3$. 5-Amino-2,4,6-triiodo-3-[N-(2-hydroxyethyl)aminocarbonyl]benzoic acid or the acid chloride is used to produce compounds wherein $R_2$ equals $NHCH_2CH_2OH$. In the latter case, the hydroxyl group is preferably protected during later steps by means of an acetate group as described above.

The intermediate compounds may be prepared from 5-nitroisophthalic acid monomethyl ester via well-established synthetic routes. See, for example, U.S. Pat. No. 3,290,366, incorporated herein by reference, and European Application 0 308 364.

Examples of such compounds, wherein $R_2$ does not equal $R_1$, are [N-(2,3-dihydroxypropyl)-N-(2-hydroxyethyl)]-DL-5-α-hydroxypropionylamino-2,4,6-triiodo-3-N-methylaminocarbonylbenzamide, [N-(2,3-dihydroxypropyl)-N-(2-hydroxyethyl)]-5-hydroxyacetylamino-2,4,6-triiodo-3-N-methylaminocarbonylbenzamide, [N-(2,3-dihydroxypropyl)-N-(2-hydroxyethyl)]-DL-5-α-hydroxypropionylamino-2,4,6-triiodo-3-N-(2-hydroxyethyl)aminocarbonylbenzamide, [N-(2,3-dihydroxypropyl)-N-(2-hydroxyethyl)]-3-N-(2-hydroxyethylaminocarbonyl)-5-hydroxyacetylamino-2,4,6-triiodobenzamide, [N-(2,3-dihydroxypropyl)-N-(2-hydroxyethyl)]-DL-5-(N-methyl-α-hydroxypropionylamino)-2,4,6-triiodo-3-N-methylaminocarbonylbenzamide, [N-(2,3-dihydroxypropyl)-N-(2-hydroxyethyl)]-5-(N-methyl-2-hydroxyacetylamino)-2,4,6-triiodo-3-N-methylaminocarbonylbenzamide, [N-(2,3-dihydroxypropyl)-N-(2-hydroxyethyl)]-DL-5-(N-methyl-α-hydroxypropionylamino-2,4,6-triiodo-3-N-(2-hydroxyethyl)aminocarbonylbenzamide, [N-(2,3-dihydroxypropyl)-N-(2-hydroxyethyl)]-3-N-(2-hydroxyethylaminocarbonyl)-5-(N-methyl-2-hydroxyacetylamino-2,4,6-triiodobenzamide, [N-(2,3-dihydroxypropyl)-N-(2-hydroxyethyl)]-DL-5-(N-2-hydroxyethyl-α-hydroxypropionylamino)-2,4,6-triiodo-3-N-methylaminocarbonylbenzamide, [N-(2,3-dihydroxypropyl)-N-(2-hydroxyethyl)]-5-(N-2-hydroxyethyl-2-hydroxyacetylamino)-2,4,6-triiodo-3-N-methylaminocarbonylbenzamide, [N-(2,3-dihydroxypropyl)-N-(2-hydroxyethyl)]-DL-5-(N-2-hydroxyethyl-α-hydroxypropionylamino)-2,4,6-triiodo-3-N-(2-hydroxyethyl)aminocarbonylbenzamide, [N-(2,3-dihydroxypropyl)-N-(2-hydroxyethyl)]-3-N-(2-hydroxyethylaminocarbonyl)-5-(N-2-hydroxyethyl-2-hydroxyacetylamino)-2,4,6-triiodobenzamide, [N-(2,3-dihydroxypropyl)-N-(2-hydroxyethyl)]-DL-5-N-butyrolactamido-2,4,6-triiodo-3-N-methylaminocarbonylbenzamide, [N-(2,3-dihydroxypropyl)-N-(2-hydroxyethyl)]-5-N-butyrolactamido-2,4,6-triiodo-3-N-methylaminocarbonylbenzamide, [N-(2,3-dihydroxypropyl)-N-(2-hydroxyethyl)]-DL-5-N-butyrolactamido-2,4,6-triiodo-3-N-(2-hydroxyethyl)aminocarbonylbenzamide, and [N-(2,3-dihydroxypropyl)-N-(2-hydroxyethyl)]-3-N-(2-hydroxyethylaminocarbonyl)-5-N-butyrolactamido-2,4,6-triiodobenzamide.

Examples of the dimeric compounds of the present invention wherein $R_2$ equals $R_1$ are N,N'-bis[3,5-bis(N-2,3-dihydroxypropyl-N-2-hydroxyethylaminocarbonyl)-2,4,6-triiodophenyl]malondiamide; N,N'-bis[3,5-bis(N-2,3-dihydroxypropyl-N-2-hydroxyethylaminocarbonyl)-2,4,6-triiodophenyl]oxamide; and N,N'-bis[3,5-bis(N-2,3-dihydroxypropyl-N-2-hydroxyethylaminocarbonyl)-2,4,6-triiodophenyl]succinamide.

These compounds may be prepared by first forming a dimer by reacting two moles of 5-amino-2,4,6-triiodoisophthaloyl chloride under amide-forming conditions with one mole of a diacid chloride such as oxalyl chloride, malonyl chloride, or succinyl chloride. 3-(N-2-Hydroxyethyl)amino-1,2-propanediol is then reacted with the intermediate dimer to form the compounds of the present invention.

Examples of dimeric compounds of the present invention wherein $R_2$ does not equal $R_1$ are N,N'-bis[3-(N-2-hydroxyethylaminocarbonyl) -5-(N-2,3-dihydroxypropyl-N-2-hydroxyethylaminocarbonyl)-2,4,6-triiodophenyl]-malondiamide; N,N'-bis[3-(N-2-hydroxyethylaminocarbonyl) -5-(N-2,3-dihydroxypropyl-N-2-hydroxyethylaminocarbonyl)-2,4,6-triiodophenyl]-oxamide; N,N'-bis[3-(N-2-hydroxyethylaminocarbonyl) -5-(N-2,3-dihydroxypropyl-N-2-hydroxyethylaminocarbonyl)-2,4,6-triiodophenyl]-succinamide; N,N'-bis[3-(N-2,3-dihydroxypropylaminocarbonyl) -5-(N-2,3-dihydroxypropyl-N-2-hydroxyethylaminocarbonyl)-2,4,6-triiodophenyl]-oxamide; N,N'-bis[3-(N-2,3-dihydroxypropylaminocarbonyl) -5-(N-2,3-dihydroxypropyl-N-2-hydroxyethylaminocarbonyl)-2,4,6-triiodophenyl]-malondiamide; N,N'-bis[3-(N-2,3-dihydroxypropylaminocarbonyl) -5-(N-2,3-dihydroxypropyl-N-2-hydroxyethylaminocarbonyl)-2,4,6-triiodophenyl]-succinamide; N,N'-dimethyl-N,N'-bis[3-(N-2-hydroxyethylaminocarbonyl) -5-(N-2,3-dihydroxypropyl-N-2-hydroxyethylaminocarbonyl)-2,4,6-triiodophenyl]-malondiamide; N,N'-dimethyl-N,N'-bis[3-(N-2-hydroxyethylaminocarbonyl) -5-(N-2,3-dihydroxypropyl-N-2-hydroxyethylaminocarbonyl)-2,4,6-triiodophenyl]-oxamide; N,N'-dimethyl-N,N'-bis[3-(N-2-hydroxyethylaminocarbonyl) -5-(N-2,3-dihydroxypropyl-N-2-hydroxyethylaminocarbonyl)-2,4,6-triiodophenyl]-succinamide; N,N'-dimethyl-N,N'-bis[3-(N-2,3-dihydroxypropyl-aminocarbonyl) -5-(N-2,3-dihydroxypropyl-N-2-hydroxyethylaminocarbonyl)-2,4,6-triiodophenyl]-oxamide; N,N'-dimethyl-N,N'-bis[3-(N-2,3-dihydroxypropylaminocarbonyl) -5-(N-2,3-dihydroxypropyl-N-2-hydroxyethylaminocarbonyl)-2,4,6-triiodophenyl]-malondiamide; and N,N'-dimethyl-N,N'-bis[3-(N-2,3-dihydroxypropylaminocarbonyl) -5-(N-2,3-dihydroxypropyl-N-2-hydroxyethylaminocarbonyl)-2,4,6-triiodophenyl]-succinamide.

These compounds are prepared by first making the desired R, substitution and then forming the dimer by reaction with the desired diacid chloride, such as oxalyl chloride, malonyl chloride, or succinyl chloride. The amino-alcohol is then added under amide-forming conditions. If secondary substitution of the diamide nitrogens is desired, i.e., when $R_5$ is other than hydrogen, this step is performed last. Examples of compounds which may be used to add the desired substituents under basic, alkylating conditions are alkyl halides, for example, methyl halides, such as methyl iodide; 2-haloethylacetates, such as 2-bromoethylacetate; 2-haloethanols, such as 2-chloroethanol; and 2-haloethyl methyl ethers, such as 2-bromoethyl methyl ether.

The reactions necessary to produce the compounds of the present invention may be carried out at any convenient temperature and pressure, such as at atmospheric pressure and ambient temperatures. It is preferred that amidation and alkylation reactions be performed at such ambient temperatures. It is preferred that hydrolysis steps be carried out at elevated temperatures to achieve a sufficient rate of hydrolysis, such as at temperatures between 90° and 100° C.

Purification of the compounds of the present invention is desired for their use as X-ray contrast agents. Purification may be by standard isolation methods, such as crystallization, or by preparative HPLC, such as by reverse-phase HPLC, or combinations of these.

The following examples of the practice of the present invention are meant to be illustrative and are in no way limiting the scope of the invention.

EXAMPLE 1

Preparation of 5-Amino-2,4,6-triiodoisophthaloyl chloride

5-Amino-2,4,6-triiodoisophthalic acid (234.5 g, 0.42 g-mole) is slurried in 200 ml of ethylacetate at 50° C. Thionyl chloride (399.3 g, 243.8 ml, 3.36 g-mole) is added dropwise over a 1 hour period. The temperature is then increased to 68° C., and the contents are stirred for 7 hours, and then for an additional 16 hours at room temperature (20°-25° C.). EtOAc and excess thionyl chloride are partially removed by vacuum distillation (vacuum, 35° C. pot temperature) to leave a yellow paste. This paste is stirred with 200 ml 1,1,1-trichloroethane (TCE) at 0°-5° C. for 1 hour, and collected by suction filtration while cold. The fine yellow powder is washed twice with 100 ml cold 1,1,1-TCE, filtered and dried in a vacuum desiccator to give the desired product (12.5 g, 50% yield). The product develops as one spot by TLC(EtOAc/MeOH/HOAc; 10/5/1), and its $^{13}C$ nmr spectrum is consistent with the structure.

EXAMPLE 2

Preparation of N,N'-bis[(2,3-dihydroxypropyl)-2-hydroxyethyl]-5-acetamido-2,4,6-triiodoisophthalamide A. 5-Acetamido-2,4,6-triiodoisophthaloyl chloride 5-Amino-2,4,6-triiodoisophthaloyl chloride (190 g, 0.32 g-mole) prepared as in Example 1 is dissolved in 475 ml of N,N-dimethylacetamide (DMAc) (dried over molecular sieves), and the solution is stirred and cooled to 0°-3° C. Acetyl chloride (75.1 g, 68 ml, 0.96 g-mole) is added dropwise over a period of 100 minutes, keeping the temperature between 0° C. and 3° C. The ice bath is removed and the solution is stirred overnight at room temperature (20°-25° C.). An additional charge of acetyl chloride (8.5 g, 0.11 g-mole) is added, and the mixture is stirred overnight (23 hours). The product (a creamy white sold) precipitates during this time. The mixture is cooled to 0°-5° C. and filtered while cold. After rinsing with three 100-ml portions of hexane on the funnel, the solution is stirred with three 200-ml portions of cold hexane for 10 minutes each time, collected by suction filtration, and dried in a vacuum desiccator (183 g, 90% yield). The product shows one major spot by TLC analysis.

B. N,N'-bis[(2,3-dihydroxypropyl)-2-hydroxyethyl]-5-acetamido-2,4,6-triiodoisophthalamide.

A mixture of 5-acetamido-2,4,6-triiodoisophthaloyl chloride (92.0 g, 0.14 g-mole) and anhydrous $Na_2CO_3$ (38 g, 0.36 g-mole) in a flask containing 200 ml of dry DMAc is immersed in an ice bath. At a temperature of 0°-5° C., 3-(N-2-hydroxyethyl)amino-1,2-propanediol (48 g, 0.36 g-mole) (96 ml of a 50% w/v DMAc solution) is added dropwise with stirring over a period of 1 hour, keeping the temperature below 5° C. The mixture is stirred for 1 additional hour at 0°-5° C., then stirred for 48 hours at room temperature (20°-25° C.). The mixture is filtered to remove the inorganic salts; the DMAc is removed by rotary evaporation (high vacuum, 80° C.) to leave an orange-yellow gum (78.14 g). The gum is dissolved in water to make 250 ml of solution (pH 10.5) and passed through a bed of IRA-118H strong cation exchange resin (62 ml, 1.3 meq./ml). The resin is then washed with two 100 ml portions of water; the washes and the eluent are combined and evaporated to provide an off-white foam (49.8 g). The product is purified by reverse-phase preparative HPLC to give 37.5 g of a white glassy solid (a 31% yield having a purity of 99.6% by HPLC). The $^{13}C$ nmr spectrum is consistent with the structure. [Calculated % composition for $C_{20}H_{28}I_3N_3O_9$; C: 28.76; H: 3.38; N: 5.03; I: 45.58. Found: C: 28.31; H: 3.40; N: 5.04; I: 45.80.] The water solubility (w/v) is 100%; the i.v. $LD_{50}$ in mice is 13.8 g I/kg; the osmolality is 590 mOsm/Kg, 32%I.

EXAMPLE 3

Preparation of N,N'-Bis[(2,3-dihydroxypropyl)-2-hydroxyethyl]-5-hydroxyacetamido-2,4,6-triiodoisophthalamide

A. 5-Acetoxyacetamido-2,4,6-triiodoisophthaloyl chloride 59.6 g (0.1 g-mole) of 5-amino-2,4,6-triiodoisophthaloyl chloride prepared as in Example 1, is dissolved in 100 ml of DMAc and 27.3 g (0.2 g-mole) of acetoxyacetyl chloride is added as the solution temperature is maintained at 25°-35° C. After the addition, the solution is allowed to stir and heated at 35°-40° C. for 4 hours to complete the reaction. The solution is cooled to room temperature and poured slowly into 1 L of cold water (0°-5° C.) with stirring to precipitate the product.

The white solid is filtered, washed with cold water and dried, giving 69 g (99% yield) of the desired product. The product shows one spot by TLC analysis (EtOAc/CH$_2$Cl$_2$; 30/20). The $^{13}C$ nmr data are consistent with the structure.

B. 5-Acetoxyacetamido-N,N'-bis(2,3-dihydroxypropyl)-2-hydroxyethyl]-2,4,6-triiodoisophthalamide 69 g (0.1 g-mole) of 5-acetoxyacetamido-2,4,6-triiodoisophthaloyl chloride is dissolved in DMAc (140 ml) and anhydrous Na$_2$CO$_3$ (31.8 g, 0.3 g-mole) is added. To the solution, a DMAc solution (87 ml) containing 26.2 g (0.3 g-mole) of 3-(N-2-hydroxyethyl)amino-1,2-propanediol is added. The mixture is heated and stirred at 35°-40° C. until the reaction is completed as determined by the TLC analysis (EtOAc/CH$_2$Cl$_2$; 30/20). After the reaction, the inorganic salts are filtered and the filtrate containing the desired product is evaporated to dryness to give a gum. The gum is triturated with isopropyl alcohol to dissolve the excess amino-triol. The clear supernatant is decanted and the residual solid is dissolved in water (150 ml), treated with Amberlite ® IR-120H resin and evaporated to dryness to give the desired product (77 g, 86% yield).

C. N,N'-Bis(2,3-dihydroxypropyl)-2-hydroxyethyl]-5-hydroxyacetamido-2,4,6-triiodoisophthalamide 5-Acetoxyacetamido-N,N'-bis[(2,3-dihydroxypropyl)-2-hydroxyethyl]-2,4,6-triiodoisophthalamide (77 g, 0.086 g-mole) is dissolved in 270 ml of hot water containing 8.2 g (0.08 g-mole) sulfuric acid. The solution is stirred and heated at 95°-100° C. to hydrolyze the acetate. At the end of the reaction, the solution is cooled to room temperature and deionized using an anionic exchange resin, IRA-93 (Rohm and Haas Co.) to remove sulfuric acid. The solution is then concentrated and the crude product is purified by preparative liquid chromatography to provide the purified desired product (51 g; 0.06 g-mole, 70% yield). The $^{13}C$ nmr spectra are consistent with the structure. The HPLC purity is 99.1% (C$_{18}$, H$_2$O/MeOH; 95/5). The water solubility (w/v) is 100%; the iv $LD_{50}$ in mice is 5 g I/kg (based on iodine content). Osmolality: 676 mOsm/kg (32% I); viscosity: 8.2 cps (37°), 10.0 cps (25°) (32% I).

EXAMPLE 4

Preparation of N,N'-Bis[(2,3-dihydroxypropyl)-2-hydroxyethyl]-5-(2-hydroxy)propionamido-2,4,6-triiodoisophthalamide.

This compound is prepared in the same manner as described in Example 3 starting from 5-amino-2,4,6-triiodoisophthaloyl chloride and (+)-2-acetoxypropionyl chloride.

EXAMPLE 5

Preparation of N,N'-Bis[(2,3-dihydroxypropyl)-2-hydroxyethyl]-5-(2-hydroxy)propionamido-2,4,6-triiodoisophthalamide, D- and L- optical isomers.

The D- and L- individual optical isomer of the title compound is prepared in the same manner as described in Example 4 from 5-amino-2,4,6-triiodoisophthaloyl chloride and the D- and L- optical isomer of 2-acetoxypropionyl chloride.

EXAMPLE 6

Preparation of N,N'-Bis[(2,3-dihydroxypropyl)-2-hydroxyethyl]-5-methoxyacetamido-2,4,6-triiodoisophthalamide.

A. 5-Methoxyacetamido-2,4,6-triiodoisophthaloyl chloride

5-Amino-2,4,6-triiodoisophthaloyl chloride prepared in Example 1 (59.6 g, 0.1 g-mole) is dissolved in DMAc (100 ml). The solution is cooled to 5° C. and methoxyacetyl chloride (21.7 g 0.2 g-mole) is added slowly keeping the temperature at 5°-10° C. When the addition is complete, the reaction mixture is allowed to warm to room temperature and stirred until the reaction is complete. The solution is cooled to room temperature and poured slowly into 1 L of cold water (0°-5° C.) with stirring to precipitate the product.

The white solid is filtered, washed with cold water and dried to provide the desired product.

B. N,N'-Bis](2,3-dihydroxypropyl)-2-hydroxyethyl]-5-methoxyacetamido-2,4,6-triiodoisophthalamide 5-Methoxyacetamido-2,4,6-triiodoisophthaloyl chloride (56.7 g, 0.085 g-mole) and anhydrous Na$_2$CO$_3$ (18 g, 0.17 g-mole) are mixed in DMAc (70 ml). A solution of DMAc (57 ml) containing 3-(N-2-hydroxyethyl)amino-1,2-propanediol (34.5 g, 0.255 g-mole) is added. The mixture is allowed to stir at 35°-40° C. until the reaction is complete. The mixture is then filtered to remove the inorganic salts and the filtrate containing the desired product is evaporated to give a gum. The material is triturated with isopropyl alcohol to dissolve the excess aminoalcohol. The clear supernatant is decanted and the residual solid is evaporated to dryness to give the crude product. The crude product is dissolved in water and purified by reverse-phase preparative HPLC to provide the purified product.

EXAMPLE 7

Preparation of N,N'-Bis[(2,3-dihydroxypropyl)-2-hydroxyethyl]-5-[N-(2-hydroxyethyl)hydroxyacetamido]-2,4,6-triiodoisophthalamide.

A.

5N-(2-Acetoxyethyl)acetoxyacetamido1-N,N'-bis(2,3-dihydroxypropyl)
-2-hydroxyethyl]-2,4,6-triiodoisophthalamide 5-Acetoxyacetamido-N,N'-bis[(2,3-dihydroxypropyl)-2-hydroxyethyl]-2,4,6-triiodoisophthalamide, prepared as in Example 3, Step B, (89 g, 0.1 g-mole) is mixed with $K_2CO_3$ (27.6 g, 0.2-g mole) and 2-bromoethyl acetate (33.4 g, 0.2 g-mole) in DMAc (200 ml). The mixture is stirred at 35°–40° C. until the reaction is complete (approximately 8-12 hours). The solution is then cooled to room temperature and the inorganic salts are filtered. The filtrate is then evaporated under vacuum at 70° C. to yield a thick oil. The oil is triturated with isopropyl alcohol to dissolve the residual DMAC and bromoethyl acetate. The supernatant is decanted and the residual solid is evaporated to dryness to provide the desired product.

B.
N,N'-Bis[(2,3-dihydroxypropyl)-2-hydroxyethyl]-5-[2-hydroxyethyl)hydroxyacetamido]-2,4,6-triiodoisophthalamide.

This compound is prepared from the hydrolysis of the product of Step A as described in Example 3, Step C.

EXAMPLE 8

Preparation of N,N'-Bis[(2,3-dihydroxypropyl)-2-hydroxyethyl]-5-[N-(2-hydroxyethyl)acetamido]-2,4,6-triiodoisophthalamide 5-Acetamido-N,N'-bis[(2,3-dihydroxypropyl)-2-hydroxyethyl]-2,4,6-triiodoisophthalamide, prepared as in Example 2, Step B, (83.5 g, 0.1 g-mole) is dissolved in 1 N NaOH (140 ml, 0.14 g-mole) and the solution is stirred at room temperature for 1 hour and 2-chloroethanol (13.7 g, 0.17 g-mole) is added. The solution is stirred at 50° C. for 5 hours to complete the reaction. The solution is acidified with $H_2SO_4$ and evaporated to dryness under reduced pressure. The residue is triturated with MeOH and the precipitated solid is filtered. The mother liquor is concentrated under vacuum and the crude product is purified by reverse-phase ($C_{18}$) HPLC to give the purified final product. The yield of this reaction and purification is 80%.

EXAMPLE 9

Preparation of N,N'-Bis[(2,3-dihydroxypropyl)-2-hydroxyethyl]-5-[N-(2-methoxyethyl)acetamido]-2,4,6-triiodoisophthalamide This compound is prepared from 5-acetamido-N,N'-bis[(2,3-dihydroxypropyl)-2-hydroxyethyl]-2,4,6-triiodoisophthalamide, prepared as in Example 2, Step B, with 2-bromoethyl methyl ether ($BrCH_2CH_2OCH_3$) in the same manner as described in Example 8.

EXAMPLE 10

Preparation of N,N'-Bis[(2,3-dihydroxypropyl)-2-hydroxyethyl]-5-(N-methyl)hydroxyacetamido-2,4,6-triiodoisophthalamide N,N'-Bis[(2,3-dihydroxypropyl)-2-hydroxyethyl]-5-hydroxyacetamido-2,4,6-triiodoisophthalamide, prepared as in Example 3, Step C, (85.1 g, 0.1 g-mole) is dissolved in 200 ml of water and 110 ml of 1N NaOH (0.11 g-mole) is added. The solution is stirred at room temperature for 1 hour and evaporated to dryness under vacuum. The residue is then dissolved in 100 ml of DMAc and the solution is warmed to 35° C. Methyl iodide (17 g, 0.12 g-mole) is added dropwise and the solution is stirred at 35° C. for 12-16 hours until the reaction is complete as monitored by HPLC. The solution is evaporated and the residue is dissolved in water. The solution is then treated with a cationic ion-exchange resin, e.g., Amberlite ® IR-120H (Rohm & Haas Co.) to remove the salts. The solution is evaporated and the material is purified by reverse-phase HPLC to yield the purified desired material.

EXAMPLE 11

Preparation of N,N'-Bis[(2,3-dihydroxypropyl)-2-hydroxyethyl]-5-N-methylacetamido-2,4,6-triiodoisophthalamide This compound is prepared from 5-acetamido-N,N'-bis[2,3-dihydroxypropyl)-2-hydroxyethyl]-2,4,6-triiodoisophthalamide in the same manner as described in Example 10.

EXAMPLE 12

Preparation of N,N'-Bis[(2,3-dihydroxypropyl)-2-hydroxyethyl]-5-N-(2-hydroxybutyrolactamido)-2,4,6-triiodoisophthalamide

A.

5-Amino-N,N'-bis(2-acetoxyethyl)(2,3-diacetoxypropyl]-2,4,6-triiodoisophthalamide 5-Amino-2,4,6-triiodoisophthaloyl chloride prepared as in Example 1 (59.6 g, 0.1 g-mole), and anhydrous $Na_2CO_3$(31.8 1 g, 0.3 g-mole) are mixed in DMAc (200 ml). A solution of DMAc (100 ml) containing 3-(N-2-hydroxyethyl)amino-1,2-propanediol (40.5 g, 0.3 g-mole) is added slowly and the mixture is allowed to stir at 35°–40° C. overnight. The mixture is then filtered to remove the inorganic salts. The filtrate is evaporated under vacuum and the gummy residue is triturated with isopropyl alcohol to effect the precipitation of the product. The solid is collected and dried to provide 5-amino-N,N'-bis[(2,3-dihydroxypropyl)-2-hydroxyethyl]-2,4,6-triiodoisophthalamide.

This compound (79 g, 0.1 g-mole) is slurried in pyridine, and acetic anhydride (71.4 g, 0.7 g-mole) is added dropwise with stirring and cooling so that the reaction temperature is maintained at <30° C. After the addition, the mixture is allowed to stir at room temperature overnight to complete the reaction.

The reaction solution is diluted with EtOAc (350 ml); ice water (350 ml) is added and the mixture is stirred for 30 minutes. A mixture of cold water (350 ml) and conc. HCl (70 ml) is added and the mixture is stirred for 30 minutes. The layers are separated and the organic layer is collected, washed with diluted HCl (two×100 ml) and 10% NaCl solution (100 ml). The organic layer is then dried over anhydrous $Na_2SO_4$ and evaporated under reduced pressure to give the desired product. The product shows one spot by the analysis ($EtOAc/CH_2Cl_2$,30/20); HPLC purity: >97% yield: 99 g (95%).

B. 2,4-Dibromobutyryl bromide

This compound is prepared according to the general procedure in *Org. Syn. Coll. Vol. V.* p. 255, incorporated herein by reference. In a 2 L flask equipped with an addition funnel, a mechanical stirrer, a thermometer and a reflux condenser are placed 40 g of red phosphorous and 300 g of butyrolactone. The system is connected to a gas trap through the condenser. The reaction mixture is cooled with an ice bath. Bromine (188.4 mL, 584 g) is added over 35 minutes. The reaction mixture reaches a maximum temperature of 54° C. The reaction mixture is warmed to 70° C. with a steam bath. The remaining bromine (188.4 mL, 584 g) is added while the reaction is cooled with an ice bath to keep its temperature between 70°-80° C. The reaction mixture is heated with a steam bath to 80° C. for 3 hours. The steam bath is turned off and nitrogen is bubbled through the reaction mixture for 3.5 hours to drive out hydrogen bromide and excess bromine. A slow stream of nitrogen is bubbled through the reaction mixture over night. The reaction mixture is filtered through glass wool to remove the gummy residue. It is distilled at 155°-170° C. under vacuum (1.5 to 0.7 mm) to give 958.17 g (89% yield) of light yellow 2,4-dibromobutyryl bromide. Its NMR spectrum is consistent with its structure.

C. N,N'-Bis(2-acetoxyethyl)-2,3-diacetoxypropyl]-5-N-(2,4-dibromobutyramido)-2,4,6-triiodoisophthalamide 2,4-Dibromobutyryl bromide (92 g, 0.3 g-mole) is placed into a flask equipped with a mechanical stirrer, a thermometer and a drying tube. The compound prepared in Step A (78.5 g, 0.075 g-mole) in DMAc (200 ml) is added while the reaction mixture is cooled to room temperature with an ice bath. The mixture is stirred at room temperature until the reaction is complete. The mixture is then poured slowly into 1 L of ice water and the mixture is stirred for 30 minutes as a solid form. The aqueous mixture is extracted 3 times with EtOAc (500 ml each). The combined EtOAc extracts are washed with water (500 ml), saturated $NaHCO_3$ solution (two times 200 ml), water (400 ml) and saturated NaCl solution (200 ml). The organic layer was dried over anhydrous $Na_2SO_4$ and the solvent was evaporated under reduced pressure to provide the crude desired product to be used in the next step.

D. 5-N-(2-Bromobutyrolactamido)-N,N'-bis[2,3-dihydroxypropyl)-2-hydroxyethyl]-2,4,6-triiodoisophthalamide Crude product prepared in Step C (94 g, 0.074 g-mole) is dissolved in 450 ml of methanol in flask equipped with a mechanical stirrer. Sodium hydroxide (50%) solution (76 ml) is diluted with 450 ml of water and added into the methanol solution with cooling (ice-bath). After the addition, the cooling is removed and the solution is stirred for 1.5 hours to complete the reactions (hydrolysis of the acetate and the cyclization). The reaction mixture is then acidified to pH 3 with hydrochloric acid. The solution is concentrated to about 400 ml and ethanol (600 ml) is added to precipitate the inorganic salts. The salts are filtered off and the filtrate is evaporated to dryness under reduced pressure to provide the crude product. The crude product is dissolved in water (45 g in 50 ml) and purified by prep HPLC to give 28 g of purified desired product (40% yield).

E. N,N'-Bis[2,3-dihydroxypropyl)-2-hydroxyethyl]-5-N-(2-hydroxybutyrolactamido)-2,4,6-triiodoisophthalamide The compound prepared in Step D (28 g, 0.03 g-mole), distilled ethanol (500 ml) and potassium acetate (11.8 g, 0.12 g-mole) are mixed in a 2 L flask equipped with a mechanical stirrer, a reflux condenser and a thermometer. The mixture is refluxed until the reaction is complete. The solvent is removed under vacuum and a solid is obtained. The solid is dissolved in water (200 ml) and the solution is treated with 150 g of pre-washed mixed-bed ion-exchange resins. After stirring for 15 minutes, the resins are filtered off and the solution is evaporated under vacuum to give a foamy solid of crude product. The material is dissolved in water (40 ml) and purified by preparative HPLC to give 8 g of the purified product as an overall 32% yield.

EXAMPLE 13

Preparation of N,N'-Bis[(2,3-dihydroxypropyl)-2-hydroxyethyl]-5-N-(S-2-hydroxybutyrolactamido)-2,4,6-triiodoisophthalamide

A. DL-2-Acetoxy-4-(methylthio)butyric acid

Calcium 2-hydroxy-4-(methylthio)butyrate (33.8 g, 0.1 g-mole) and acetyl chloride (110 g) are refluxed in a 250 ml round-bottom flask for 2.5 hours. The mixture is evaporated to a syrup and treated with 150 ml acetone. The brown mixture is stirred for 30 minutes, filtered, and the filtrate evaporated to dryness to give 37 g, 96.4% of brown viscous oil which is identified by TLC and nmr.

B. Resolution of DL-2-Acetoxy-4-(methylthio)butyric acid

Resolution is accomplished with brucine. Thus, a solution of the mixed isomers 486 g (2.53 mol) in 500 ml ethanol, is filtered in a 12 L resin pot and treated with a hot filtered solution of brucine, 1 kg, (2.53 mol, Sigma Chemical) in 3 L of ethanol. The precipitate formed is left overnight at room temperature, filtered, washed with 2 L of ethanol and 1 L of ether to yield 900 g material. This is crystallized from 6 L of ethanol to give 640 g solid, m.p. 184°-186° C., and then recrystallized once more from ethanol, 6L, to give 570 g solid, 38.3%, m.p. 185°-187° C., [α]−31° (1% H₂O).

The free acid is released from the brucine salt by dissolving 570 g of the solid obtained above in 5.5 L water in a 12 L resin pot. This is treated with concentrated HCl to pH 0.7 (200 ml), and the pale brown solution is extracted twice with 2.5 L ethyl acetate. The extract is washed with water, three times 300 ml, dried over anhydrous sodium sulfate, evaporated to dryness to give brown thick oil, 182.2 g, 97.8% [α]−33.78° (0.1258 g in 10 ml CHCl₃).

C. Verification of Optical Purity

This preparation is made in order to verify optical purity of the above compound as generally disclosed at Angew. Che. Int. Ed. 18. 797 (1979); and J. Am. Chem. Soc. 78, 2429 (1956), incorporated herein by reference.

L-2-Hydroxy-4-(methylthio)butyric acid and acetylation

In a 1 L, 3-necked flask is dissolved L-2-amino-4-(methylthio)butyric acid (14.9 g, 0.1 g-mole) in aqueous H₂SO₄ solution (80 ml) and cooled to −5° C. This is treated with a solution of NaNO₂ in 30 ml water. The mixture is stirred overnight at room temperature and extracted with three times 100 ml ether, dried over anhydrous Na₂SO₄ and evaporated to dryness to give an oil, 1.4 g 9.3%. TLC shows one major spot and IR is in agreement with the structure. Acetylation of the compound (1.5 g, 0.01 mol) is carried out with acetyl chloride (0.07 mol, 6.5 ml); the mixture was refluxed for 1 hour, evaporated to dryness and the residue dissolved in CHCl₃. This is extracted three times with 30 ml NaHCO₃ solution (5%), washed twice with 30 ml CHCl₃, filtered and acidified with concentrated HCl (pH 1). The precipitated oil is extracted with chloroform, washed with 30 ml water, dried over anhydrous Na₂SO₄ and evaporated to dryness to give brown oil, 1.76 g (91.6%).

The brucine salt is prepared by dissolving 1.1 g (0.0057 ml) of the above material L-2-acetoxy-4-(methylthio)butyric acid, in 10 ml EtOH and treatment with a hot filtered solution of brucine (0.0057 mol, 2.26 g in ethanol, 20 ml). The salt obtained is filtered and recrystallized from ethanol (40 ml) three times to obtain pure salt, m.p. 184°-186° C. [α]−31° (1% H₂O), identical in m.p., mixed m.p. (undepressed), and optical rotation to compound prepared in Steps A and B.

D. L-2-Acetoxy-4-(methylthio)butyryl chloride

In a 1 L, 3-necked flask is dissolved 173 g of compound prepared in (Step B) in 500 ml CH₂Cl₂, cooled in ice-methanol bath and treated with SOCl₂ (120 g) followed by 3 ml DMF. The mixture is stirred overnight at room temperature. The solvent is distilled and the residue purified by distillation at 84°-86° C. (0.1–0.05 mm Hg) to give pale yellow oil 157 g, 83%. IR and nmr data are consistent with the structure for the desired acid chloride.

E. N,N'-Bis2-Acetoxyethyl-2,3-diacetoxypropyl]-5-N-[(S-2-acetoxy-4-methylthiobutyramido)]-2,4,6-triiodoisophthalamide 5-Amino-N,N'-bis[(2-acetoxyethyl)(2,3-diacetoxypropyl)]-2,4,6-triiodoisophthalamide, prepared as in Example 12, Step A, (200 g, 0.2 g-mole) is dissolved in DMAc (175 ml) and cooled in ice-methanol bath and treated with the acid chloride prepared in Step D (84.2 g, 0.4 g-mole) in 84 ml DMAc. The solution is stirred at room temperature overnight and then poured over a solution of sodium bicarbonate (50.4 g, 0.6 g-mole) in 750 ml water and filtered. The solid is washed with 100 ml water twice and dried to give a glassy material of the desired compound (241 g, 99% yield).

F. N,N'-Bis[2-Acetoxyethyl-2,3-diacetoxypropyl]-5-N-(S-2-acetoxy-4-methylthiobutyramido)]-2,4,6-triiodoisophthalamide, methyl iodide A solution of the compound prepared in Step E (232 g, 0.19 g-mole) in DMF (475 ml) is stirred with methyl iodide (165 g, 11.6 g-mole) at room temperature overnight. The mixture is evaporated to dryness and the residue triturated with three times 1 L ether. The residue is dissolved in acetone (170 ml) and the product is precipitated with the treatment of cold ether. The crystals are filtered, washed with ether to obtain a nearly quantitative yield of the desired compound (255 g).

G. N,N'-Bis[(2 3-Dihydroxypropyl)-2-hydroxyethyl]-5-N-(S-2-hydroxybutyrolactamido)-2,4,6-triiodoisophthalamide A solution of the compound prepared in Step F (136 g, 0.1 g-mole) in 500 ml of MeOH and NaOH solution (80 g in 640 ml water) are mixed while cooling with ice-water. The mixture is stirred at room temperature overnight and then treated with 65 ml of AcOH. Methanol is removed under reduced pressure and the solution is treated with mixed-bed ion-exchange resins. The solution is filtered and concentrated to provide the crude product. The crude product is dissolved in water and purified by preparative HPLC (C₁₈, water as the mobile phase) to provide the purified material.

EXAMPLE 14

Preparation of 5-N-Butyrolactamido-N,N'-bis[(2,3-dihydroxypropyl)-2-hydroxyethyl]-2,4,6-triiodoisophthalamide

A. N,N'Bis[(2-acetoxyethyl)-2,3-diacetoxypropyl]-5-(4-chlorobutyramido)-2,4,6-triiodoisophthalamide In a flask equipped with a mechanical stirrer, dropping funnel, thermometer and drying tube, 5-amino-N,N'-bis[(2-acetoxyethyl)(2,3-diacetoxypropyl)]-2,4,6-triiodoisophthalamide, prepared as in Example 12, Step A, (48 g, 0.046 g-mole) is dissolved in DMAc (120 ml). The solution is cooled to 15° C. and 4-chlorobutyryl chloride (13 g, 0.092 g-mole) is added slowly with stirring. The reaction solution is then stirred at room temperature until the reaction is completed as determined by tlc.

The solution is poured into 1 L of ice-water with stirring. A gummy material precipitates. After stirring for 10 minutes, EtOAc (350 ml plus 150 ml twice) is added to dissolve the gum and extract the solution. The combined EtOAc solution is washed with water (200 ml), 5% NaHCO₃ (two times 200 ml), saturated NaCl solution (two times 150 ml), dried over anhydrous Na₂SO₄ (100 g) and evaporated to give a crude solid product. Without further purification, the crude product is utilized in the following step.

B.
5-N-Butyrolactamido-N,N'-bis](2,3-dihydroxypropyl)-2,4,6-triiodoisophthalamide The crude compound prepared in Step A (18.4 g, 0.016 g-mole) is suspended in MeOH (100 ml) in a flask equipped with a mechanical stirrer, an addition funnel and a thermometer. The suspension is cooled to 10° C. and NaOH solution (98 ml of 1N solution) is added slowly so the temperature is maintained at 10°-20° C. When 25 ml of NaOH solution is added, the suspension became a clear solution. After the addition, the cooling (ice-bath) is removed and the solution is stirred at room temperature overnight.

The solution is stirred with Amberlite IR-120H resin (120 ml) for 2 hours and filtered. The filtrate is evaporated to dryness to give the crude desired product at a quantitative yield. The purification of the product is carried out by preparative HPLC using $C_{18}$ column and $H_2O$/MeOH as the mobile phase. The elutions containing the desired product are combined and evaporated to dryness to provide the purified product (8.2 g, 60% yield).

EXAMPLE 15

Preparation of
[N-(2,3-dihydroxypropyl)-N-(2-hydroxyethyl]-DL-5-α-hydroxypropionylamino-2,4,6-triiodo-3-N-methylaminocarbonylbenzamide

A.
DL-5-α-Acetoxypropionylamino-2,4,6-triiodo-3-N-methylaminocarbonylbenzoyl chloride 5-Amino-2,4,6-triiodo-3-N-methylaminocarbonylbenzoyl chloride (59 g, 0.1 g-mole) is slurried in DMAc (110 ml) at 35°-40° C. DL-2-Acetoxypropionyl chloride (30.2 g, 0.2 g-mole) is added dropwise keeping the temperature at 40°-48° C. The slurry is stirred at 40° C. for 30 minutes, turning into a clear brown solution. After stirring overnight at 40° C., HPLC analysis indicates complete reaction. The solution is slowly poured into 1.1 L of cold water (0°-5° C.) with stirring. A creamy, white solid precipitates. It is collected, washed three times with 50 ml water, and dried to give the desired product (62.4 g, 88.6% yield) as confirmed by TLC and nmr.

B.
DL-5-α-Acetoxypropionylamino-N-(2,3-dihydroxypropyl)
-N-(2-hydroxyethyl)]-2,4,6-triiodo-3-N-methylaminocarbonylbenzamide The compound prepared in Step A (60 g, 0.085 g-mole) is added to a mixture of 3-(N-2-hydroxyethyl)amino-1,2-propanediol dissolved in DMAc (23 g, 0.17 g-mole, in 56.4 ml solution, 40.87% w/v), additional DMAc (70 ml) and sodium carbonate (18 g, 0.17 g-mole) at 40° C. The mixture is stirred at room temperature for 20 hours, then warmed to 40° C. for 5 hours, and again stirred overnight at room temperature. The mixture is filtered and the solid collected and washed twice with 50 ml DMAc. The filtrate and washes are combined and evaporated to give a thick oil (105.8 g). The oil is triturated with 200 ml isopropyl alcohol, yielding some solid and again with 700 ml acetone, yielding more solid. The supernatant is decanted and the solid washed with 200 ml acetone. The acetone is decanted and the solid evaporated to dryness, yielding 32 g of crude, desired product. The combined decantations, isopropyl alcohol and acetone, are evaporated to yield a thick oil, which when triturated with 100 ml acetone yields a gummy solid. The solid is dried, yielding 44 g crude product, for a combined yield of 76 g.

C.
[N-(2,3-dihydroxypropyl)-N-(2-hydroxyethyl)-DL-5-α-hydroxypropionylamino-2,4,6-triiodo-3-N-methylaminocarbonyl]benzamide The crude product prepared in Step B (theoretically 0.085 g-mole) is dissolved in 300 ml water (pH 9.2). Conc. $H_2SO_4$ (5 ml) is added to adjust the pH to 1. The solution is refluxed for 7 hours and then evaporated to dryness. The gummy solid remaining is dissolved in 300 ml water and the solution is stirred at 100° C. overnight. HPLC analysis showed approx. 80% purity. The solution is then treated with ion exchange resins IRA-68, IRA-458, and IR-120 H, 100 ml each, and the resins are washed four times each with 100 ml water. The washings and solution are combined and evaporated to dryness giving a yellow glassy solid (48 g, 80.5% pure). The crude product is then purified by reverse-phase preparative HPLC to yield 34 g. The structure was verified by nmr. The product is 100% water soluble. The i.v. $LD_{50}$ in mice is 13.1 g I/kg. Osmolality: 506 mOsm/kg (32% I); viscosity: 4.9 cps (37°), 8.1 cps (25°) (32% I).

EXAMPLE 16

Preparation of
[N-(2,3-dihydroxypropyl)-N-(2-hydroxyethyl)]-5-hydroxyacetylamino-2,4,6-triiodo-3-N-methylaminocarbonylbenzamide

A.
5-Acetoxyacetylamino-2,4,6-triiodo-3-N-methylaminocarbonylbenzoyl chloride 5-Amino-2,4,6-triiodo-3-N-methylaminocarbonylbenzoyl chloride (61 g, 0.1033 g-mole) is added to DMAc (100 ml) with stirring and heated to 30° C. Acetoxyacetyl chloride is added slowly with stirring. After stirring at 40° C. for 4 hours and overnight at room temperature, the product completely solidifies from the solution. Tetrahydrofuran (200 ml) is added and the slurry stirred for 1 hour at room temperature. The white solid is filtered, washed three times with THF (30-40 ml) and dried under vacuum at 50° C. to produce the crude, desired product.

B.
5-Acetoxyacetylamino-[N-(2,3-dihydroxypropyl)-N-(2-hydroxyethyl)]-2,4,6-triiodo-3-N-methylaminocarbonylbenzamide The crude product of Step A (theoretically 0.1033 g-mole) is added to a mixture of 3-(N-2-hydroxyethyl)amino-1,2-propanediol (28 g dissolved in 110 ml DMAc) and sodium bicarbonate (17.7 g, 0.21 g-mole) with stirring and heating to 55° C. Carbon dioxide evolution occurs. After stirring at 55°-60° C. for five hours, the solution is allowed to stir overnight at room temperature and filtered. The solid is washed three times with 50 ml methanol, and the washings are combined with the filtrate. The combined solution is evaporated under vacuum at 70° C. yielding a thick oil. The oil is triturated with 500 ml isopropyl alcohol at 65° C. for 30 minutes and then allowed to cool. The supernatant is decanted. The residue is again triturated with 350 ml isopropyl alcohol and then allowed to cool. The supernatant is decanted and the residue evaporated to dryness under vacuum at 75° C. yielding the desired product (57 g, 70% yield), confirmed by nmr.

C.
[N-(2,3-dihydroxypropyl)-N-(2-hydroxyethyl)1-5-hydroxyacetylamino-2,4,6-triiodo-3-N-methylaminocarbonylbenzamide The product of Step B is hydrolyzed and purified as in Example 15, Step C, yielding 10.8 g, 99.8% pure. However, the solubility in water (w/v) was found to be less than 25%.

EXAMPLE 17
Preparation of
[N-(2,3-dihydroxypropyl)-N-(2-hydroxyethyl)]-5-[(hydroxyacetyl)(2-hydroxyethyl)amino]-2,4,6-triiodo-3-N-methylaminocarbonylbenzamide The title compound is prepared by hydrolysis of [N-(2,3-dihydroxypropyl)-N-(2-hydroxyethyl)]-5-(acetoxyacetyl)(2-acetoxyethyl)amino]-2,4,6-triiodo-3-N-methylaminocarbonylbenzamide by a procedure similar to the hydrolysis of Example 15, Step C. The diacetate is prepared by reacting 5-acetoxyacetylamino-[N-(2,3-dihydroxypropyl)-N-(2-hydroxyethyl)]-2,4,6-triiodo-3-N-methylaminocarbonylbenzamide (prepared as in Example 16, Steps A and B) with 2-bromoethylacetate in DMSO in the presence of a base such as potassium carbonate.

EXAMPLE 18
Preparation of
[N-(2,3-dihydroxypropyl)-N-(2-hydroxyethyl)]-5-(2-hydroxyacetyl)amino-2,4,6-triiodo-3-N-(2-hydroxyethyl)aminocarbonylbenzamide

A.
3-[N-(2-Acetoxyethyl)aminocarbonyl]-5-amino-2,4,6-triiodobenzoic acid

To a stirred solution of 5-amino-2,4,6-triiodo-3-N-(2-hydroxyethyl)aminocarbonylbenzoic acid (107.24 g, 0.178 g-mole) in anhydrous DMAc (100 ml) containing a catalytic amount of 4-dimethylaminopyridine (600 mg, 5 mmoles) is added acetic anhydride (29.10 g, 0.285 g-mole, 1.6 equiv.) dropwise over 20 minutes at room temperature. Stirring is continued at room temperature for 16 hours and then 200 ml water is added with vigorous stirring. The resulting suspension is filtered, and the collected solids washed with 100 ml water and dried in a vacuum oven (70° C., 140 mm Hg) for 24 hours to yield 98.23 g (86% yield) desired product. The product exhibits one spot by tlc employing a solvent system of ethyl acetate/methanol (95:5, v/v). $^1$H and $^{13}$C nmr spectra are consistent with the assigned structure.

B.
3-[N-(2-Acetoxyethyl)aminocarbonyl]-5-amino-2,4,6-triiodobenzoyl chloride To the product of Step A (75.0 g, 0.117 g-mole) is added thionyl chloride (207.9 g, 1.75 g-mole, 15 equiv.) with stirring at room temperature. The resulting solution is heated to reflux with stirring for 3 hours. Excess thionyl chloride is removed by distillation under reduced pressure, partly as an azeotrope with THF (200 ml). The residue is taken up in methylene chloride (1 L) and washed with water (250 ml), saturated aqueous sodium bicarbonate solution (250 ml), and saturated aqueous sodium chloride solution (100 ml). The organic solution is separated, dried over anhydrous sodium sulfate, filtered, and concentrated under vacuum to yield the desired product (74.25 g, 96% yield). The product exhibited one spot by tlc employing a solvent system of ethyl acetate/hexane (70:30 v/v). $^1$H and $^{13}$C nmr spectra are consistent with the structure.

C.
5-Acetoxyacetylamino-3-N-(2-acetoxyethyl)aminocarbonyl-2,4,6-triiodobenzoyl chloride To a solution of the product of Step B (60 g, 0.091 g-mole) in DMAc (60 ml) is added acetoxyacetyl chloride (24.73 g, 0.18 g-mole, 2 equiv.) with stirring over 20 minutes at room temperature. Stirring is continued at room temperature for 16 hours and the reaction mixture then added to vigorously stirred ice cold water. The resulting solid product is collected by vacuum filtration and dried in a vacuum oven to yield 66.95 g (96% yield) of the desired product, confirmed by tlc and nmr.

D.
[N-(2,3-Dihydroxypropyl)-N-(2-hydroxyethyl)1-5-(acetoxyacetylamino)-2,4,6-triiodo-3-N-(acetoxyethyl)-aminocarbonylbenzamide To a solution of the product of Step C (66.65 g, 0.087 g-mole) in DMAc (60 ml) containing anhydrous sodium carbonate (9.22 g, 0.087 g-mole, 1 equiv.) is added 3-(N-2-hydroxyethyl)amino-1,2-propanediol (43.5 ml of a 41% w/v solution in DMAc, 1.5 equiv.) with stirring at room temperature under an atmosphere of dry nitrogen. After stirring at room temperature for 16 hours, the mixture is filtered through celite to remove inorganic salts and then distilled under high vacuum. This yields 102.8 g of crude product.

E.
[N-(2,3-Dihydroxypropyl)-N-(2-hydroxyethyl]-5-(2-hydroxyacetyl)amino-2,4,6-triiodo-3-N-(2-hydroxyethyl)aminocarbonylbenzamide The crude diacetate product of Step D is dissolved in methanol (90 ml) and water (90 ml) is added. The pH is adjusted to 1 with sulfuric acid, and the mixture is stirred and heated to reflux for 2 hours. The mixture is then concentrated by distillation and purified by passing it through ion-exchange resins and by preparative HPLC, yielding 25.77 g of 98% pure product as confirmed by HPLC, tlc, and nmr. The product is 100% w/v water-soluble. Osmolality: 597 mOsm/kg (32% I); viscosity: 5.3 cps (37°), 7.4 cps (25°) (32% I); the i.v. LD50 in mice is 20.6 gI/kg.

EXAMPLE 19
Preparation of
[N-(2,3-dihydroxypropyl)-N-(2-hydroxyethyl)]-3-N-(2-hydroxyethyl)aminocarbonyl-DL-5-α-hydroxypropionylamino-2,4,6-triiodobenzamide As in Example 18, the title compound is prepared stepwise by reacting the product of Example 18, Step B with (±)-2-acetoxypropionyl chloride, as in Step C and completing the synthesis.

EXAMPLE 20

Preparation of
[N-(2,3-dihydroxypropyl)-N-(2-hydroxyethyl)]-5-N-(2-hydroxybutyrolactamido)-2,4,6-triiodo-3-N-methylaminocarbonylbenzamide As in Example 12, the title compound is prepared stepwise by first reacting 5-amino-2,4,6-triiodo-3-N-methylaminocarbonylbenzoyl chloride with 3-(N-2-hydroxyethyl)amino-1, 2-propanediol dissolved in DMAc in the presence of sodium carbonate. The product, 5-amino[N-(2,3,-dihydroxypropyl)-N-(2-hydroxyethyl]-2,4,6-triiodo-3-N-methylaminocarbonylbenzamide, is reacted with acetic anhydride in the presence of pyridine to produce the triacetate, [N-(2-acetoxyethyl)-N-(2,3-diacetoxypropyl)]-5-amino-,4,6-triiodo -3-N-methylaminocarbonylbenzamide. This compound is then reacted with 2,4-dibromobutryl bromide, prepared as in Example 12, Step B, and the product is then cyclized, hydrolyzed, and purified as in Example 12, Steps D and E to produce the final product.

EXAMPLE 21

Preparation of
[N-(2,3-dihydroxypropyl)-N-(2-hydroxyethyl)]-5-N-(2-hydroxybutyrolactamido)-2,4,6-triiodo-3-[N-(2-hydroxyethyl) aminocarbonyl]benzamide The title compound is prepared as in Examples 12 and 19 starting from 3-N-(2-acetoxyethyl)aminocarbonyl-5-amino-2,4,6-triiodobenzoyl chloride.

EXAMPLE 22

Preparation of
N,N'-bis[3,5-bis(N-2,3-dihydroxypropyl-N-2-hydroxyethyl)aminocarbonyl]-2,4,6-triiodophenyl]-malondiamide A.
N,N'-bis[3,5-bis(chlorocarbonyl)-2,4,6-triiodophenyl]-malondiamide 5-Amino-2,4,6-triiodoisophthaloyl chloride (59.58 g, 0.1 g-mole) is dissolved in 130 ml dioxane (dried over molecular sieves). The solution is heated to 90° C. and stirred while malonyl chloride (8.5 g, 0.06 g-mole) is added dropwise. The mixture was stirred at 90° C. for 3 hours. A pasty precipitate forms. The solid is filtered, washed three times with 25 ml dioxane on the filter, suction-dried and then vacuum dried at 60° C. to yield the desired product (51.4 g, 81% yield). The structure of the dimer was confirmed by nmr.

B.
N,N'-Bis[3,5-bis(N-2,3-dihydroxypropyl-N-2-hydroxyethylaminocarbonyl)-2,4,6-triiodophenyl]-malondiamide The product of Step A (50 g, 0.04 g-mole) is added slowly to a mixture of 3-(N-2-hydroxyethyl)amino-1,2-propanediol (32.4 g, 0.24 g-mole) dissolved in DMAc (115 ml) and sodium carbonate (17 g, 0.16 g-mole), with stirring. After 7 hours stirring at room temperature, the reaction is complete as determined by HPLC. The reaction mixture is diluted with 200 ml DMAc and filtered to remove the salts. The clear filtrate is evaporated to dryness yielding a clear yellow gummy solid (86.5 g). The solid is triturated with 50 ml isopropanol at 60° C. for 10 minutes. After standing overnight the supernatant is decanted and the solid evaporated to dryness. The solid is dissolved in 150 ml water at 60°-65° C. yielding a clear solution, pH 10. The solution is stirred with Amberlite IR-120 plus H resin for 30 minutes (pH 1-2) and filtered. The filtrate is evaporated to dryness to give the crude desired product (61.4 g, 95% purity by HPLC). The crude product is purified by preparative reverse-phase HPLC, yielding 37 g (56% yield) having 985 purity. The compound is 100% (w/v) water soluble. Osmolality: 213 mOsm/kg (32% I), 191 mOsm/kg (28% I); viscosity: 18.8 cps (37°, 32% I), 11.4 cps (37°, 28% I); the i.v. $LD_{50}$ in mice: 17.5 gI/kg.

EXAMPLE 23

Preparation of
N,N'-bis[3,5-bis(N-2,3-dihydroxypropyl-N-2-hydroxyethyl)aminocarbonyl]-2,4,6-triiodophenyl]-oxamide.

This compound is prepared as in Example 22 using oxalyl chloride in place of malonyl chloride.

EXAMPLE 24

Preparation of
N,N'-Bis[3,5-bis(N-2,3-dihydroxypropyl-N-2-hydroxyethylaminocarbonyl) -2,4,6-triiodophenyl]-succinamide This compound is prepared as in Example 22 using succinyl chloride in place of malonyl chloride.

EXAMPLE 25

Preparation of
N,N'-Bis[3-(N-2-hydroxyethylaminocarbonyl) -5-(N-2,3-dihydroxypropyl-N-2-hydroxyethylaminocarbonyl)-2,4,6-triiodophenyl]-oxamide The title compound is prepared by reacting 3-N-(2-acetoxyethyl)aminocarbonyl -5-amino-2,4,6-triiodobenzoyl chloride, prepared as in Example 18, Step B, with oxalyl chloride in dioxane; reacting that product with 3-(N-2-hydroxyethyl)amino-1,2-propanediol in DMAc; and hydrolyzing the acetate groups with aqueous sulfuric acid (as in Example 18, Step E).

EXAMPLE 26

Preparation of
N,N'-Bis[3-(N-2-hydroxyethylaminocarbonyl) -5-(N-2,3-dihydroxypropyl-N-2-hydroxyethylaminocarbonyl)-2,4,6-triiodophenyl]-malondiamide The title compound is prepared as in Example 25 using malonyl chloride instead of oxalyl chloride.

EXAMPLE 27

Preparation of
N,N'-Bis[3-(N-2-hydroxyethylaminocarbonyl) -5-(N-2,3-dihydroxypropyl-N-2-hydroxyethylaminocarbonyl)-2,4,6-triiodophenyl]-succinamide The title compound is prepared as in Example 25 using succinyl chloride instead of oxalyl chloride.

EXAMPLE 28

Preparation of
N,N'-Bis[3-(N-2,3-dihydroxypropionaminocarbonyl) -5-(N-2,3-dihydroxypropyl-N-2-hydroxyethylaminocarbonyl) -2,4,6-triiodophenyl]-malondiamide This compound is prepared by reacting two equivalents of 5-amino-3-(N-2,3-diacetoxypropionaminocarbonyl)-2,4,6-triiodobenzoyl chloride with malonyl chloride, then reacting the dimer with two equivalents of 3-(N-2-hydroxyethyl)amino-1,2-propanediol, and finally removing the acetate groups by hydrolysis.

EXAMPLE 29

Preparation of
N,N'-Bis[3-(N-2,3-dihydroxypropionaminocarbonyl)
-5-(N-2,3-dihydroxypropyl-N-2-hydroxyethylaminocarbonyl)-2,4,6-triiodophenyl]-oxamide The title compound is prepared as in Example 28 using oxalyl chloride instead of malonyl chloride.

EXAMPLE 30

Preparation of
N,N'-Bis[3-(N-2,3-dihydroxypropionaminocarbonyl)
-5-(N-2,3-dihydroxypropyl-N-2-hydroxyethylaminocarbonyl)-2,4,6-triiodophenyl]-succinamide The title compound is prepared as in Example 28 using succinyl chloride instead of malonyl chloride.

EXAMPLE 31

Preparation of
N,N'-dimethyl-N,N'-bis[3,5-bis(N-2,3-dihydroxypropyl-N-2-hydroxyethyl)aminocarbonyl]-2,4,6-triiodophenyl]-malondiamide The title compound is prepared by reacting the product of Example 22 with methyl iodide under basic, alkylating conditions.

EXAMPLE 32

Preparation of
N,N'-dimethyl-N,N'-bis[3,5-bis(N-2,3-dihydroxypropyl-N-2-hydroxyethyl)aminocarbonyl]-2,4,6-triiodophenyl]-oxamide The title compound is prepared by reacting the product of Example 23 with methyl iodide under basic, alkylating conditions.

EXAMPLE 33

Preparation of
N,N'-dimethyl-N,N'-bis[3,5-bis(N-2,3-dihydroxypropyl-N-2-hydroxyethyl)aminocarbonyl]-2,4,6-triiodophenyl]-succinamide The title compound is prepared by reacting the product of Example 24 with methyl iodide under basic, alkylating conditions.

EXAMPLE 34

Preparation of
N,N'-dimethyl-N,N'-Bis[3-(N-2-hydroxyethylaminocarbonyl)
-5-(N-2,3-dihydroxypropyl-N-2-hydroxyethylaminocarbonyl)-2,4,6-triiodophenyl]-oxamide The title compound is prepared by reacting the product of Example 25 with methyl iodide under basic, alkylating conditions.

EXAMPLE 35

Preparation of
N,N'-dimethyl-N,N'-Bis[3-(N-2-hydroxyethylaminocarbonyl)
-5-(N-2,3-dihydroxypropyl-N-2-hydroxyethylaminocarbonyl)-2,4,6-triiodophenyl]-malondiamide The title compound is prepared by reacting the product of Example 26 with methyl iodide under basic, alkylating conditions.

EXAMPLE 36

Preparation of
N,N'-dimethyl-N,N'-Bis[3-(N-2-hydroxyethylaminocarbonyl)
-5-(N-2,3-dihydroxypropyl-N-2-hydroxyethylaminocarbonyl)-2,4,6-triiodophenyl]-succinamide The title compound is prepared by reacting the product of Example 27 with methyl iodide under basic, alkylating conditions.

EXAMPLE 37

Preparation of
N,N'-dimethyl-N,N'-bis[3-(N-2,3-dihydroxypropionamino-carbonyl)
-5-(N-2,3-dihydroxypropyl-N-2-hydroxyethylaminocarbonyl)-2,4,6-triiodophenyl]-malondiamide The title compound is prepared by reacting the product of Example 28 with methyl iodide under basic, alkylating conditions.

EXAMPLE 38

Preparation of
N,N'-dimethyl-N,N'-bis[3-(N-2,3-dihydroxypropionamino-carbonyl)
-5-(N-2,3-dihydroxypropyl-N-2-hydroxyethylaminocarbonyl)-2,4,6-triiodophenyl]-oxamide The title compound is prepared by reacting the product of Example 29 with methyl iodide under basic, alkylating conditions.

EXAMPLE 39

Preparation of
N,N'-dimethyl-N,N'-bis[3-(N-2,3-dihydroxypropionamino-carbonyl)
-5-(N-2,3-dihydroxypropyl-N-2-hydroxyethylaminocarbonyl)-2,4,6-triiodophenyl]-succinamide The title compound is prepared by reacting the product of Example 30 with methyl iodide under basic, alkylating conditions.

EXAMPLE 40

Preparation of
3-(N-2-hydroxyethyl)amino-1,2-propanediol (Two methods)

A. Glycidol (128 g, 115 ml, 1.73 g-mole) is added dropwise over a 1 hour period to ethanolamine (854 g, 843 ml, 14.0 g-mole) with stirring, keeping the temperature below 10° C. After the addition is complete, the temperature is allowed to rise to room temperature and the solution is stirred for 20 hours. TLC analysis of the yellow solution indicates the reaction is complete. The product is separated from the excess ethanolamine by Kugelrohr distillation (b.p. 170°-182° C. at 1-1.2 mm Hg) to give a colorless thick oil which solidifies on standing (196 g, 84% yield). $^{13}C$ nmr spectrum and elemental analysis data are consistent with the structure.

B. 3-Chloro-1,2-propanediol (110.5 g, 1 g-mole) is added dropwise over a 3 hour period to ethanolamine (305.4 g, 5.0 g-mole) with stirring. The temperature of the reaction is kept at 10°-15° C. After the addition is complete, the solution is allowed to warm to room temperature, then stirred overnight. The excess ehtanolamine is removed by Kugelrohr distillation to yield 145 g of a thick oil, the hydrochloride salt of the desired product. The oil is dissolved in 160 ml water. To this solution is added 50% w/w NaOH solution (44.21 ml, 33.8 g, 0.85 g-mole), with stirring, keeping the temperature below 20° C. After the addition is complete, the solution is stirred overnight at room temperature. Water is removed by rotary evaporation (80° C., under vacuum) to yield an orange oil. The oil is dissolved in 125 ml of methanol to precipitate sodium chloride. The salt is filtered off and the filtrate is evaporated to yield 98.3 g of an orange oil. The desired product is isolated from this oil by Kugelrohr distillation (148°-168° C., 0.8-0.9 mm Hg) to give a colorless oil which solidifies on standing (71 g, 53% yield). $^{13}$C nmr data are consistent with the structure.

What is claimed is:

1. A compound of the formula:

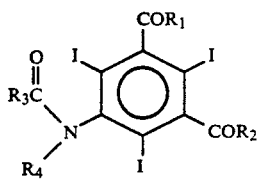

wherein $R_1$ is $N(CH_2CH_2OH)CH_2CHOHCH_2OH$; $R_2$ equals $NHCH_3$, $NHCH_2CH_2OH$, or $NHCH_2CHOHCH_2OH$; $R_3$ equals $CH_3$, $CH_2OH$, $CH(CH_3)OH$, $CHOHCH_2OH$, $CH_2OCH_3$, or $CH_2OCH_2CH_3$; $R_4$ equals H, $CH_3$, $CH_2CH_2OH$, $CH_2CH_2OCH_3$, $CH_2CHOHCH_2OH$, or $CH_2CHOHCH_2OCH_3$; or $R_3$ and $R_4$ together form the group

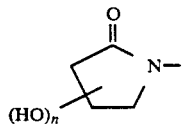

wherein n equals 0-3.

2. A compound of the formula

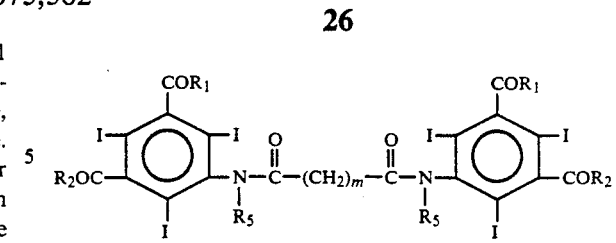

wherein $R_1$ is $N(CH_2CH_2OH)CH_2CHOHCH_2OH$; $R_2$ equals $NHCH_3$, $NHCH_2CH_2OH$, or $NHCH_2CHOHCH_2OH$; $R_5$ is H, $CH_3$, $CH_2CH_2OH$, $CH_2CHOHCH_2OH$, or $CH_2OCH_3$; and m equals 0-4.

3. The compound of claim 1, wherein $R_2$ is selected from the group consisting of $NHCH_3$, $NHCH_2CH_2OH$, and $NHCH_2CHOHCH_2OH$.

4. The compound of claim 1, wherein $R_4$ is hydrogen.

5. The compound of claim 1, wherein $R_4$ is selected from the group consisting of $CH_3$, $CH_2CH_2OH$, $CH_2CH_2OCH_3$, $CH_2CHOHCH_2OH$, and $CH_2CHOHCH_2OCH_3$.

6. The compound of claim 2, wherein $R_2$ equals $NHCH_2CHOHCH_2OH$ and m equals 0.

7. The compound of claim 2, wherein $R_2$ equals $NHCH_2CHOHCH_2OH$ and m equals 1.

8. The compound of claim 2, wherein $R_2$ equals $NHCH_2CHOHCH_2OH$ and m equals 2.

9. The compound of claim 2, wherein $R_2$ is selected from the group consisting of $NHCH_3$, $NHCH_2CH_2OH$, and $NHCH_2CHOHCH_2OH$.

10. The compound of claim 1 wherein $R_1$ is $N(CH_2CH_2OH)CH_2CHOHCH_2OH$; $R_2$ is $NHCH_2CH_2OH$, $R_3$ is $CH_2OH$ and $R_4$ is H.

11. The compound [N-(2,3-Dihydroxypropyl)-N-(2-hydroxyethyl)]-5-(2-hydroxyacetyl) amino-2,4,6-triiodo-3-N-(2-hydroxyethyl)aminocarbonylbenzamide.

12. The compound of claim 1 wherein $R_1$ is $N(CH_2CH_2OH)CH_2CHOHCH_2OH$; $R_2$ is $NHCH_2CHOHCH_2OH$; $R_3$ is $CH_2OH$ and $R_4$ is H.

13. The compound [N-(2,3-Dihydroxypropyl)-N-(2-hydroxyethyl)]-3-N-(2,3-dihydroxypropyl-aminocarbonyl) -5-(2-hydroxyacetyl)amino-2,4,6-triiodobenzamide.

* * * * *

UNITED STATES PATENT AND TRADEMARK OFFICE
CERTIFICATE OF CORRECTION

PATENT NO. : 5,075,502
DATED : December 24, 1991
INVENTOR(S) : Mills T. KNELLER et al.

It is certified that error appears in the above-indentified patent and that said Letters Patent is hereby corrected as shown below:

Claim 1, Column 25, line 32, delete "; or $R_3$";

delete lines 33-41 in their entirety; and line 42, delete "wherein n equals 0-3".

Signed and Sealed this

Sixth Day of June, 1995

Attest:

BRUCE LEHMAN

Attesting Officer      Commissioner of Patents and Trademarks